(12) United States Patent
Carrette et al.

(10) Patent No.: US 9,139,512 B2
(45) Date of Patent: Sep. 22, 2015

(54) ABSORBENT SOLUTION CONTAINING A DEGRADATION INHIBITOR DERIVED FROM A TRIAZOLE OR FROM A TETRAZOLE AND METHOD OF ABSORBING ACID COMPOUNDS CONTAINED IN A GASEOUS EFFLUENT

(75) Inventors: P.-Louis Carrette, Lyons (FR); Bruno Delfort, Paris (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 906 days.

(21) Appl. No.: 13/387,119

(22) PCT Filed: Jul. 6, 2010

(86) PCT No.: PCT/FR2010/000492
§ 371 (c)(1),
(2), (4) Date: Feb. 24, 2012

(87) PCT Pub. No.: WO2011/012777
PCT Pub. Date: Feb. 3, 2011

(65) Prior Publication Data
US 2012/0148463 A1 Jun. 14, 2012

(30) Foreign Application Priority Data
Jul. 31, 2009 (FR) ...................... 09 03812

(51) Int. Cl.
*B01D 53/40* (2006.01)
*B01D 53/77* (2006.01)
(Continued)

(52) U.S. Cl.
CPC .......... *C07C 215/08* (2013.01); *B01D 53/1475* (2013.01); *B01D 53/1493* (2013.01); *C07C 213/10* (2013.01); *B01D 53/77* (2013.01);
(Continued)

(58) Field of Classification Search
CPC ........ B01D 53/40; B01D 53/77; B01D 53/78; B01D 53/1456; B01D 53/1475; B01D 53/1493; B01D 2258/00; B01D 2258/02; B01D 2258/05; B01D 2258/06; B01D 2258/0233; B01D 2258/0283; B01D 2258/0291; B01D 2252/604; B01D 2252/2056; B01D 2252/20415; B01D 2252/20436; Y02C 10/06
USPC .......... 423/210, 228; 548/250, 251, 252, 255, 548/259, 260, 262.2, 263.2, 263.4, 268.8, 548/267.2, 268.6
See application file for complete search history.

(56) References Cited

U.S. PATENT DOCUMENTS 5,686,016 A 11/1997 Veldman et al.
6,372,793 B1 * 4/2002 Lamango et al. ............. 514/562
(Continued)

FOREIGN PATENT DOCUMENTS

EP 1 582 250 A2 10/2005
FR 2 820 430 A1 8/2002
(Continued)

*Primary Examiner* — Stanley Silverman
*Assistant Examiner* — Daniel Berns
(74) *Attorney, Agent, or Firm* — Fitch, Even, Tabin and Flannery LLP (57) ABSTRACT

The degradation of an absorbent solution comprising organic compounds with an amine functional group in aqueous solution is substantially reduced in the presence of a small amount of degradation inhibiting agents belonging to the family of derivatives of triazoles or of a tetrazole at least one substituent of which contains a sulfur atom. The absorbent solution is used to deacidize a gaseous effluent.

15 Claims, 3 Drawing Sheets

(51) Int. Cl.
*B01D 53/78* (2006.01)
*B01D 53/14* (2006.01)
*C07D 249/00* (2006.01)
*C07D 249/04* (2006.01)
*C07D 249/08* (2006.01)
*C07D 249/10* (2006.01)
*C07D 249/12* (2006.01)
*C07D 257/04* (2006.01)
*C07C 215/08* (2006.01)
*C07C 213/10* (2006.01)

(52) U.S. Cl.
CPC ..... *B01D2252/604* (2013.01); *B01D 2257/302* (2013.01); *B01D 2257/304* (2013.01); *B01D 2257/306* (2013.01); *B01D 2257/308* (2013.01); *B01D 2257/504* (2013.01); *B01D 2258/00* (2013.01); *B01D 2258/05* (2013.01); *B01D 2258/06* (2013.01); *Y02C 10/06* (2013.01)

(56) References Cited

U.S. PATENT DOCUMENTS 7,056,482 B2 6/2006 Hakka et al.
2006/0204433 A1* 9/2006 Carrette et al. ............ 423/574.2

FOREIGN PATENT DOCUMENTS

FR 2 909 010 A1 5/2008
FR 2909010 * 5/2008 ............. B01D 53/14

* cited by examiner

ABSORBENT SOLUTION CONTAINING A DEGRADATION INHIBITOR DERIVED FROM A TRIAZOLE OR FROM A TETRAZOLE AND METHOD OF ABSORBING ACID COMPOUNDS CONTAINED IN A GASEOUS EFFLUENT

FIELD OF THE INVENTION

The present invention relates to the sphere of deacidizing a gaseous effluent. More precisely, the present invention provides compounds for reducing the degradation of an absorbent solution intended to absorb the acid compounds contained in a gaseous effluent, the absorbent solution comprising amines in aqueous solution. In particular, the invention relates to compounds used to reduce the degradation of the amines used for deacidizing gases containing oxygen, such as combustion fumes for example.

BACKGROUND OF THE INVENTION

Deacidizing gaseous effluents such as, for example, natural gas and combustion fumes, is generally carried out by washing with an absorbent solution. The absorbent solution allows the acid compounds present in the gaseous effluent ($H_2S$, mercaptans, $CO_2$, COS, $SO_2$, $CS_2$) to be absorbed.

Deacidizing these effluents, notably decarbonation and desulfurization, imposes specific requirements on the absorbent solution, in particular thermal and chemical stability, notably towards the impurities in the effluent, i.e. essentially oxygen, $SO_x$ and $NO_x$. The oxygen can also come into contact with the absorbent solution without being necessarily present in the gaseous effluent to be treated, for example in case of an accidental air inflow in the absorbent solution storage tanks.

Currently, the most commonly used absorbent solutions are aqueous alkanolamine solutions. Document FR-2,820, 430 provides gaseous effluent deacidizing methods.

It is however well known to the person skilled in the art that these amines involve the drawback of degrading under the conditions of use.

In particular, the amines can be degraded by oxygen, generating an amine consumption and the formation of degradation products that accumulate in the unit or, for the most volatile ones, that are carried along in the gaseous effluents of the process. Thus, in particular in the case of post-combustion fumes treatment in a process using an aqueous monoethanolamine (MEA) solution, large amounts of ammonia form. The ammonia thus formed is carried along into the atmosphere with the treated fumes, which poses environmental protection problems.

In the case of $CO_2$ capture in fumes from industrial or electric power plants or, more generally, from energy production plants, the degradation phenomena that affect amine-containing absorbent solutions are increased by the presence of massive amounts of oxygen in the feed to be treated, up to 5 vol. % in general. In the case of fumes from natural gas combined cycles, the volume proportion of oxygen in the fumes can reach 15%.

The degraded solution is characterized by:
a decrease in the absorption of the acid compounds of the feed in relation to a fresh amine solution,
an increase in the density of the absorbent solution, and in the viscosity thereof, which can lead to a performance loss,
the formation of more volatile amines that pollute the treated gas and the acid gas from the regeneration stage: ammonia, methylamine, dimethylamine and trimethyl-amine for example, depending on the nature of the amine used,
an accumulation of degradation products in the absorbent solution, which may require treating the degraded solution, possible foaming problems due to the degradation products.

The degradation of the absorbent solution thus penalizes the performance and the smooth functioning of the gas deacidizing units.

In order to overcome the degradation problem, if it is not possible to limit or to suppress the presence of oxygen in the absorbent solution, compounds whose purpose is to prevent or to limit amine compound degradation phenomena, notably the degradation generated by oxidation phenomena, are added to the absorbent solution. These compounds are commonly referred to as degradation inhibiting agents or additives. The main modes of action known for degradation inhibiting agents are, depending on the nature thereof, a reaction of reduction and/or capture, trapping and/or stabilization of the radicals formed in the absorbent solution so as to limit or to prevent or to interrupt the degradation reactions, notably chain reactions.

U.S. Pat. No. 5,686,016 mentions additives used for limiting the degradation of absorbent solutions used for deacidizing natural gas, in particular oximes.

U.S. Pat. No. 7,056,482 mentions additives used for limiting the degradation of absorbent solutions used for $CO_2$ capture, notably thiosulfates and sulfites.

In general terms, the present invention provides a family of degradation inhibiting agents that notably allows to reduce the degradation of an absorbent solution used for absorption of acid compounds contained in a gaseous effluent, the absorbent solution comprising amine compounds in aqueous solution.

SUMMARY OF THE INVENTION

The present invention describes an absorbent solution for absorbing the acid compounds contained in a gaseous effluent, said solution comprising:
a) at least one amine,
b) water,
c) at least one degradation inhibiting compound for limiting the degradation of said amine, the degradation inhibiting compound being a derivative of a triazole or of a tetrazole, at least one substituent of which comprises a sulfur atom.

According to the invention, said degradation inhibiting compound can meet one of the following general formulas:

wherein radical $R_1$ is selected from among:
a hydrogen atom,
a hydrocarbon radical comprising 1 to 12 carbon atoms,
an amino radical of general formula —$NR_4R_5$ wherein radical $R_4$ and radical $R_5$ are independently selected from among:
   a hydrogen atom,
   a hydrocarbon radical comprising 1 to 12 carbon atoms,
and wherein each radical $R_2$ and $R_3$ is independently selected from among the following elements:
a) —S—X wherein radical X is selected from among:
   a hydrogen atom,
   an alkaline or alkaline-earth element,
   a monovalent or multivalent metal,
   an ammonium cation NH4+ or resulting from the protonation of an amine function,
   a phosphonium cation,
   a hydrocarbon radical comprising 1 to 12 carbon atoms,
   a radical selected from among a thiyl-triazole, thio-triazole, thiyl-tetrazole and thio-tetrazole radical,
b) a hydrogen atom,
c) a hydroxyl radical,
d) an amino radical of general formula —$NR_4R_5$ wherein radical $R_4$ and radical $R_5$ are independently selected from among:
   a hydrogen atom,
   a hydrocarbon radical comprising 1 to 12 carbon atoms,
e) a radical comprising 1 to 12 carbon atoms.

At least one of the radicals $R_1$, $R_2$, $R_3$, $R_4$, $R_5$ and X can be a hydrocarbon group containing between 1 and 12 carbon atoms and it can additionally contain at least one compound selected from among a heteroatom and a halogen.

At least one of the radicals $R_1$, $R_2$, $R_3$, $R_4$, $R_5$ and X can comprise at least one function selected from among the group as follows: a hydroxyl function, a ketone function, a carboxylic function, an amine function and a nitrile function.

At least two radicals selected from among $R_1$, $R_2$, $R_3$, $R_4$, $R_5$ and X can be hydrocarbon groups bonded by a covalent bond so as to form a ring made up of 5, 6, 7 or 8 atoms.

The solution can comprise between 10 wt. % and 99 wt. % amine, between 1 wt. % and 90 wt. % water, and between 5 ppm and 5 wt. % degradation inhibiting compound.

The degradation inhibiting compound can be selected from among the group containing: 1H-1,2,4-triazole-3-thiol, a 1H-1,2,4-triazole-3-thiol salt, 5-phenyl-1H-1,2,4-triazole-3-thiol, a 5-phenyl-1H-1,2,4-triazole-3-thiol salt, 5-(4-pyridyl)-1H-1,2,4-triazole-3-thiol, a 5-(4-pyridyl)-1H-1,2,4-triazole-3-thiol salt, 5-(3-pyridyl)-1H-1,2,4-triazole-3-thiol, a 5-(3-pyridyl)-1H-1,2,4-triazole-3-thiol salt, 4-methyl-4H-1,2,4-triazole-3-thiol, a 4-methyl-4H-1,2,4-triazole-3-thiol salt, 4-methyl-5-(2-thienyl)-4H-1,2,4-triazole-3-thiol, a 4-methyl-5-(2-thienyl)-4H-1,2,4-triazole-3-thiol salt, 4-methyl-5-(3-thienylmethyl)-4H-1,2,4-triazole-3-thiol, a 4-methyl-5-(3-thienylmethyl)-4H-1,2,4-triazole-3-thiol salt, 4-cyclohexyl-5-sulfanyl-4H-1,2,4-triazole-3-ol, a 4-cyclohexyl-5-sulfanyl-4H-1,2,4-triazole-3-ol salt, 3-amino-1,2,4-triazole-5-thiol, a 3-amino-1,2,4-triazole-5-thiol salt, 4-amino-4H-1,2,4-triazole-3,5-dithiol, a 4-amino-4H-1,2,4-triazole-3,5-dithiol salt, [1,2,4]triazolo[4,3-a]pyridine-3-thiol, a [1,2,4]triazolo[4,3-a]pyridine-3-thiol salt, 1H-5-mercapto-1,2,3-triazole, a 1H-5-mercapto-1,2,3-triazole salt, 1-methyl-1H-tetrazole-5-thiol, a 1-methyl-1H-tetrazole-5-thiol salt, 1-ethyl-1H-tetrazole-5-thiol, a 1-ethyl-1H-tetrazole-5-thiol salt, 1-phenyl-1H-tetrazole-5-thiol, a 1-phenyl-1H-tetrazole-5-thiol salt, 1-(4-hydroxyphenyl)-1H-tetrazole-5-thiol, a 1-(4-hydroxyphenyl)-1H-tetrazole-5-thiol salt, 5-mercapto-1-tetrazolacetic acid, a 5-mercapto-1-tetrazolacetic acid salt, 1-[2-(dimethylamino)ethyl]-1H-tetrazole-5-thiol, a 1-[2-(dimethylamino)ethyl]-1H-tetrazole-5-thiol salt, 3-amino-5-methylthio-1H-1,2,4-triazole, a 3-amino-5-methylthio-1H-1,2,4-triazole salt, 5-(methylthio)-1H-tetrazole, a 5-(methylthio)-1H-tetrazole salt, 5-(ethylthio)-1H-tetrazole, a 5-(ethylthio)-1H-tetrazole salt, 1-methyl-5-(methylthio)-1H-tetrazole, a 1-methyl-5-(methylthio)-1H-tetrazole salt, 4-phenyl-4H-1,2,4-triazole-3-thiol, a 4-phenyl-4H-1,2,4-triazole-3-thiol salt, 5-methyl-4H-1,2,4-triazole-3-thiol, a 5-methyl-4H-1,2,4-triazole-3-thiol salt, 5-(trifluoromethyl)-2,4-dihydro-3H-1,2,4-triazole-3-thione, a 5-(trifluoromethyl)-2,4-dihydro-3H-1,2,4-triazole-3-thione salt, 4-isopropyl-4H-1,2,4-triazole-3-thiol and a 4-isopropyl-4H-1,2,4-triazole-3-thiol salt.

The amine can be selected from the group containing: N,N,N',N',N"-pentamethyl-diethylenetriamine, piperazine, monoethanolamine, diethanolamine, methyldiethanolamine, diisopropanolamine, diglycolamine, 2-amino-2-methylpropanol-1, a glycine salt and a taurine salt.

If the amine is selected from among monoethanolamine, diethanolamine and 2-amino-2-methylpropanol-1, the degradation inhibiting compound can be selected from among: 4-methyl-4H-1,2,4-triazole-3-thiol, 1H-1,2,4-triazole-3-thiol, 1H-5-mercapto-1,2,3-triazole, 5-mercapto-1-methyltetrazole, 5-methyl-4H-1,2,4-triazole-3-thiol, 4-isopropyl-4H-1,2,4-triazole-3-thiol, 4-phenyl-4H-1,2,4-triazole-3-thiol, 1-[2-(dimethylamino)ethyl]-1H-tetrazole-5-thiol, 4-methyl-4H-1,2,4-triazole-3-thiol sodium salt, 1H-1,2,4-triazole-3-thiol sodium salt, 1H-5-mercapto-1,2,3-triazole sodium salt, 5-mercapto-1-methyltetrazole sodium salt, 5-methyl-4H-1,2,4-triazole-3-thiol sodium salt, 4-isopropyl-4H-1,2,4-triazole-3-thiol sodium salt, 4-phenyl-4H-1,2,4-triazole-3-thiol sodium salt, 5-methyl-4H-1,2,4-triazole-3-thiol potassium salt, 4-methyl-4H-1,2,4-triazole-3-thiol potassium salt, 1H-1,2,4-triazole-3-thiol potassium salt, 4-isopropyl-4H-1,2,4-triazole-3-thiol potassium salt, 4-phenyl-4H-1,2,4-triazole-3-thiol potassium salt and 5-mercapto-1-methyltetrazole potassium salt.

The absorbent solution can comprise at least 39 wt. % monoethanolamine.

The present invention also describes a method for absorbing acid compounds contained in a gaseous effluent, wherein the gaseous effluent is contacted with an aqueous solution comprising at least one amine, and wherein the degradation of said amine is controlled by introducing at least one degradation inhibiting compound derived from a triazole or from a tetrazole, comprising at least one substituent containing a sulfur atom.

In the method according to the invention, the aqueous solution can be used for absorbing acid compounds contained in one of the effluents from the group containing natural gas, combustion fumes, syngases, refinery gases, Claus tail gases, biomass fermentation gases, cement plant gases and incinerator fumes.

The gaseous effluent can contain at least 500 vol. ppm oxygen.

At least one degradation inhibiting compound selected from among the following elements can be added to the aqueous solution: 1H-1,2,4-triazole-3-thiol, a 1H-1,2,4-triazole-3-thiol salt, 5-phenyl-1H-1,2,4-triazole-3-thiol, a 5-phenyl-1H-1,2,4-triazole-3-thiol salt, 5-(4-pyridyl)-1H-1,2,4-triazole-3-thiol, a 5-(4-pyridyl)-1H-1,2,4-triazole-3-thiol salt, 5-(3-pyridyl)-1H-1,2,4-triazole-3-thiol, a 5-(3-pyridyl)-1H-1,2,4-triazole-3-thiol salt, 4-methyl-4H-1,2,4-triazole-3-thiol, a 4-methyl-4H-1,2,4-triazole-3-thiol salt, 4-methyl-5-(2-thienyl)-4H-1,2,4-triazole-3-thiol, a 4-methyl-5-(2-thienyl)-4H-1,2,4-triazole-3-thiol salt, 4-methyl-5-(3- thienylmethyl)-4H-1,2,4-triazole-3-thiol, a 4-methyl-5-(3-thienylmethyl)-4H-1,2,4-triazole-3-thiol salt, 4-cyclohexyl-5-sulfanyl-4H-1,2,4-triazole-3-ol, a 4-cyclohexyl-5-sulfanyl-4H-1,2,4-triazole-3-ol salt, 3-amino-1,2,4-triazole-5-thiol, a 3-amino-1,2,4-triazole-5-thiol salt, 4-amino-4H-1,2,4-triazole-3,5-dithiol, a 4-amino-4H-1,2,4-triazole-3,5-dithiol salt, [1,2,4]triazolo[4,3-a]pyridine-3-thiol, a [1,2,4]triazolo[4,3-a]pyridine-3-thiol salt, 1H-5-mercapto-1,2,3-triazole, a 1H-5-mercapto-1,2,3-triazole salt, 1-methyl-1H-tetrazole-5-thiol, a 1-methyl-1H-tetrazole-5-thiol salt, 1-ethyl-1H-tetrazole-5-thiol, a 1-ethyl-1H-tetrazole-5-thiol salt, 1-phenyl-1H-tetrazole-5-thiol, a 1-phenyl-1H-tetrazole-5-thiol salt, 1-(4-hydroxyphenyl)-1H-tetrazole-5-thiol, a 1-(4-hydroxyphenyl)-1H-tetrazole-5-thiol salt, 5-mercapto-1-tetrazolacetic acid, a 5-mercapto-1-tetrazolacetic acid salt, 1-[2-(dimethyl-amino)ethyl]-1H-tetrazole-5-thiol, a 1-[2-(dimethylamino)ethyl]-1H-tetrazole-5-thiol salt, 3-amino-5-methylthio-1H-1,2,4-triazole, a 3-amino-5-methylthio-1H-1,2,4-triazole salt, 5-(methylthio)-1H-tetrazole, a 5-(methylthio)-1H-tetrazole salt, 5-(ethylthio)-1H-tetrazole, a 5-(ethylthio)-1H-tetrazole salt, 1-methyl-5-(methylthio)-1H-tetrazole, a 1-methyl-5-(methylthio)-1H-tetrazole salt, 4-phenyl-4H-1,2,4-triazole-3-thiol, a 4-phenyl-4H-1,2,4-triazole-3-thiol salt, 5-methyl-4H-1,2,4-triazole-3-thiol, a 5-methyl-4H-1,2,4-triazole-3-thiol salt, 5-(trifluoromethyl)-2,4-dihydro-3H-1,2,4-triazole-3-thione, a 5-(trifluoromethyl)-2,4-dihydro-3H-1,2,4-triazole-3-thione salt, 4-isopropyl-4H-1,2,4-triazole-3-thiol and a 4-isopropyl-4H-1,2,4-triazole-3-thiol salt.

In order to limit degradation of the monoethanolamine, the diethanolamine or the 2-amino-2-methylpropanol-1 in aqueous solution used for capturing the $CO_2$ from combustion fumes, at least one degradation inhibiting compound selected from among the group containing the following elements can be added to the aqueous solution: 4-methyl-4H-1,2,4-triazole-3-thiol, 1H-1,2,4-triazole-3-thiol, 1H-5-mercapto-1,2,3-triazole, 5-mercapto-1-methyltetrazole, 5-methyl-4H-1,2,4-triazole-3-thiol, 4-isopropyl-4H-1,2,4-triazole-3-thiol, 4-phenyl-4H-1,2,4-triazole-3-thiol, 1-[2-(dimethylamino)ethyl]-1H-tetrazole-5-thiol, 4-methyl-4H-1,2,4-triazole-3-thiol sodium salt, 1H-1,2,4-triazole-3-thiol sodium salt, 1H-5-mercapto-1,2,3-triazole sodium salt, 5-mercapto-1-methyltetrazole sodium salt, 5-methyl-4H-1,2,4-triazole-3-thiol sodium salt, 4-isopropyl-4H-1,2,4-triazole-3-thiol sodium salt, 4-phenyl-4H-1,2,4-triazole-3-thiol sodium salt, 5-methyl-4H-1,2,4-triazole-3-thiol potassium salt, 4-methyl-4H-1,2,4-triazole-3-thiol potassium salt, 1H-1,2,4-triazole-3-thiol potassium salt, 4-isopropyl-4H-1,2,4-triazole-3-thiol potassium salt, 4-phenyl-4H-1,2,4-triazole-3-thiol potassium salt and 5-mercapto-1-methyltetrazole potassium salt.

BRIEF DESCRIPTION OF THE FIGURES

Other features and advantages of the invention will be clear from reading the description hereafter, with reference to the accompanying figures wherein.

DETAILED DESCRIPTION

In order to reduce the degradation of an absorbent solution, the inventors have shown that the degradation of an absorbent solution comprising organic compounds with an amine function in aqueous solution is substantially reduced in the presence of a small amount of degradation inhibiting agents described hereafter.

The degradation inhibiting agents according to the invention are compounds belonging to the family of derivatives of triazoles or of a tetrazole at least one constituent of which contains a sulfur atom.

In the present description, triazoles are understood to be cyclic compounds with 5 atoms whose ring comprises 3 nitrogen atoms, 2 carbon atoms and 2 unsaturations, and a tetrazole is understood to be a cyclic compound with 5 atoms whose ring comprises 4 nitrogen atoms, 1 carbon atom and 2 unsaturations.

In the present description, derivatives of triazoles at least one substituent of which contains a sulfur atom means that at least one of the carbon atoms of the triazole ring is bonded to a sulfur atom by a simple bond.

In the present description, derivatives of a tetrazole at least one substituent of which contains a sulfur atom means that the carbon atom of the tetrazole ring is bonded to a sulfur atom by a simple bond.

The degradation inhibiting compounds according to the invention can for example meet the following general formulas:

Radical $R_1$ is selected from among:
a hydrogen atom,
a hydrocarbon radical comprising 1 to 12 carbon atoms, saturated or not, linear, branched or cyclic, heterocyclic or aromatic, possibly containing heteroatoms, halogens, as well as hydroxyl, ketone, carboxylic or nitrile functions,
an amino radical of general formula —$NR_4R_5$ wherein radical $R_4$ and radical $R_5$ are independently selected from among:
a hydrogen atom,
a hydrocarbon radical comprising 1 to 12 carbon atoms, preferably 1 to 3 carbon atoms, possibly containing heteroatoms, halogens, as well as hydroxyl, ketone, carboxylic or nitrile functions.

Each radical $R_2$ and $R_3$ is independently selected from among the following elements:
a) —S—X wherein radical X is selected from among:
a hydrogen atom,
an alkaline or alkaline-earth element,
a monovalent or multivalent metal,
an ammonium cation $NH_4+$ or resulting from the protonation of an amine function, a phosphonium cation, a hydrocarbon radical comprising 1 to 12 carbon atoms, saturated or not, linear, branched or cyclic, heterocyclic or aromatic, possibly containing heteroatoms, halogens, as well as hydroxyl, ketone, carboxylic, amine or nitrile functions, according to another embodiment of the invention, X can also be a thiyl-triazole or a thio-triazole radical, or a thiyl-tetrazole or a thio-tetrazole radical, substituted or not. In this case, the degradation inhibiting compound according to the invention comprises two heterocycles selected from among triazole and tetrazole, the two heterocycles being bonded to one another by two sulfur atoms, b) a hydrogen atom,
c) a hydroxyl radical,
d) an amino radical of general formula —NR$_4$R$_5$ wherein radical R$_4$ and radical R$_5$ are independently selected from among:
   a hydrogen atom,
   a hydrocarbon radical comprising 1 to 12 carbon atoms, preferably 1 to 3 carbon atoms, possibly containing heteroatoms, halogens, as well as hydroxyl, ketone, carboxylic or nitrile functions,
e) a radical comprising 1 to 12 carbon atoms, saturated or not, linear, branched or cyclic, heterocyclic or aromatic, possibly containing heteroatoms, halogens, as well as hydroxyl, ketone, carboxylic or nitrile functions.

The fact that the degradation inhibiting compound according to the invention belongs to the family of the derivatives of triazoles or of a tetrazole at least one substituent of which contains a sulfur atom leads to the fact that, in the aforementioned general formulas, at least R$_2$ or R$_3$ meets the definition of —S—X. In particular in the case of tetrazole derivatives, R$_2$ meets the definition of —S—X.

In cases where X is a multivalent alkaline-earth or metallic element, it is understood that, in order to meet the neutrality of the molecules, they can take the forms allowing them to meet this neutrality in accordance with the rules of chemistry, which can for example be illustrated as follows in one of the formulas of the invention:

with a and b integers allowing the neutrality to be met in accordance with the rules of chemistry.

According to a first embodiment, in the definition of the general formulas of the degradation inhibiting compounds according to the invention, R$_1$, R$_2$, R$_3$, R$_4$, R$_5$ and X are independent, i.e. they are not bonded to each other. However, according to a second embodiment, in cases where two elements among R$_1$, R$_2$, R$_3$, R$_4$, R$_5$ and X are hydrocarbon radicals, they can be bonded by a covalent bond to form a ring or a heterocycle, aromatic or not, made up of 5, 6, 7 or 8 atoms in accordance with the rules of chemistry.

The molecules of the invention can also exist in their form referred to as tautomeric or mesomeric when allowed, in accordance with the rules of chemistry.

The absorbent solutions according to the invention can be used to deacidize the following gaseous effluents: natural gas, syngases, combustion fumes, refinery gases, Claus tail gases, biomass fermentation gases, cement plant gases, incinerator fumes. These gaseous effluents contain one or more of the following acid compounds: $CO_2$, $H_2S$, mercaptans, COS, $SO_2$, $NO_2$, $CS_2$. In particular, the method according to the invention can be used to absorb acid compounds contained in a gaseous effluent containing oxygen, such as combustion fumes for example. The proportion of oxygen in the gaseous effluent can be above 500 vol. ppm, preferably above 0.5 vol. %, or at least 1 vol. %, 3 vol. % or 5 vol. %. In general, the proportion of oxygen in the gaseous effluent remains below 20 vol. %. The combustion fumes are produced notably by the combustion of hydrocarbons, biogas, coal in a burner or for a combustion gas turbine, for example in order to produce electricity. These fumes can contain between 50% and 90% nitrogen, and between 5% and 20% carbon dioxide. The fumes generally contain at least 500 vol. ppm, preferably at least 1 vol. %, or even 2 vol. %, 3 vol. % or 5 vol. % oxygen, up to a content that does generally not exceed 20 vol. % oxygen.

Using an absorbent solution for deacidizing a gaseous effluent generally involves an absorption stage, followed by a regeneration stage. The absorption stage consists in contacting the gaseous effluent with the absorbent solution. Upon contacting, the organic compounds having an amine function of the absorbent solution react with the acid compounds contained in the effluent so as to obtain a gaseous effluent depleted in acid compounds and an absorbent solution enriched in acid compounds. The regeneration stage notably consists in heating and optionally in expanding at least part of the acid compound-enriched absorbent solution in order to release the acid compounds in gas form. The regenerated absorbent solution, i.e. depleted in acid compounds, is recycled to the absorption stage.

The absorbent solution according to the invention comprises organic compounds in aqueous solution. Generally, the organic compounds are amines, i.e. they comprise at least one amine function. The organic compounds can come in variable concentrations, ranging for example between 10 wt. % and 99 wt. %, preferably between 20 wt. % and 75 wt. %, or even between 20 wt. % and 50 wt. % in the aqueous solution. The absorbent solution can contain between 1 wt. % and 90 wt. % water, preferably between 25 wt. % and 80 wt. %, or even between 50 wt. % and 70 wt. %.

For example, the organic compounds are amines such as N,N,N',N',N"-pentamethylethylenetriamine or piperazine. For example, piperazine is used for natural gas treatment and combustion fumes decarbonation.

The organic compounds can also be alkanolamines such as monoethanolamine (MEA), diethanolamine (DEA), methyldiethanolamine (MDEA), diisopropanolamine (DIPA), diglycolamine or 2-amino-2-methylpropanol-1 (AMP). Preferably, MDEA and DEA are commonly used for natural gas deacidizing. MEA and AMP are more particularly used for combustion fumes decarbonation.

The organic compounds can also be amino-acid salts such as glycine or taurine salts, which are notably used for $CO_2$ capture in combustion fumes.

Besides, the absorbent solution according to the invention can contain compounds that absorb physically at least partly one or more acid compounds of the gaseous effluent. For example, the absorbent solution can comprise between 5 wt. % and 50 wt. % absorbent compounds of physical character, such as methanol, sulfolane or N-formyl morpholine.

Another advantage of the invention lies in the fact that using degradation inhibiting agents according to the invention allows to increase the amine concentration commonly used by the person skilled in the art and thus to increase the performances of the method: increase in the capacity and rate of absorption of the acid compounds by the absorbent solution, leading to a decrease in the investment costs and the operating costs of the industrial unit. In fact, as shown hereafter in Example 3, in the absence of degradation inhibiting agents, the rate of degradation of the amines increases with the amine concentration increase. Thus, for example, when using an aqueous MEA (monoethanolamine) solution for capturing the $CO_2$ in combustion fumes, the MEA concentration is commonly limited to 30 wt. % so as to limit the degradation of this amine. It is understood here that the amine concentration is defined in percentage by weight in water before $CO_2$ absorption. Thus, for example, an absorbent solution used for capturing the $CO_2$ in a combustion fume and containing a degradation inhibiting agent according to the invention can contain more than 30 wt. % and preferably more than 35 wt. % MEA, a good MEA concentration value being at least 39 wt. %.

Among all the molecules belonging to the family of derivatives of the triazoles and of a tetrazole at least one constituent of which contains a sulfur atom, the following degradation inhibiting agents are preferably used: 1H-1,2,4-triazole-3-thiol, 5-phenyl-1H-1,2,4-triazole-3-thiol, 5-(4-pyridyl)-1H-1,2,4-triazole-3-thiol, 5-(3-pyridyl)-1H-1,2,4-triazole-3-thiol, 4-methyl-5-(2-thienyl)-4H-1,2,4-triazole-3-thiol, 4-methyl-5-(3-thienylmethyl)-4H-1,2,4-triazole-3-thiol, 4-cyclohexyl-5-sulfanyl-4H-1,2,4-triazole-3-ol, 3-amino-1,2,4-triazole-5-thiol, 4-amino-4H-1,2,4-triazole-3,5-dithiol, [1,2,4]triazolo[4,3-a]pyridine-3-thiol, 1H-5-mercapto-1,2,3-triazole, 1-methyl-1H-tetrazole-5-thiol, 1-ethyl-1H-tetrazole-5-thiol, 1-phenyl-1H-tetrazole-5-thiol, 1-(4-hydroxyphenyl)-1H-tetrazole-5-thiol, 5-mercapto-1-tetrazolacetic acid, 1-[2-(dimethylamino)ethyl]-1H-tetrazole-5-thiol, 3-amino-5-methylthio-1H-1,2,4-triazole, 5-(methylthio)-1H-tetrazole, 5-(ethylthio)-1H-tetrazole, 1-methyl-5-(methylthio)-1H-tetrazole, 4-phenyl-4H-1,2,4-triazole-3-thiol, 5-methyl-4H-1,2,4-triazole-3-thiol, 5-(trifluoromethyl)-2,4-dihydro-3H-1,2,4-triazole-3-thione, which is a mesomeric form of 5-(trifluoromethyl)-4H-1,2,4-triazole-3-thiol, 4-isopropyl-4H-1,2,4-triazole-3-thiol and the salts of the aforementioned elements.

The salts of the degradation inhibiting compounds according to the invention can be obtained for example by neutralization thereof, using an alkaline (preferably sodium or potassium), alkaline-earth, metal or ammonium hydroxide or carbonate, or by means of an amine present in the absorbent solution. In this case, the functions having an acid character such as, for example, the thiol functions and, for example, possibly the carboxylic acid functions, can be partly or totally neutralized.

The salts of the degradation inhibiting compounds according to the invention can also be obtained for example by neutralization thereof using an organic or inorganic acid. In this case, at least one nitrogen atom present on the molecule is protonated.

The degradation inhibiting compounds listed in the above paragraph are particularly well suited for prevention of the degradation of amines in aqueous solution used for capturing the $CO_2$ contained in combustion fumes.

In order to limit the degradation of an absorbent solution made up of amine, in particular alkanolamine, for example monoethanolamine (MEA), diethanolamine (DEA) or 2-amino-2-methylpropanol-1 (AMP), in aqueous solution notably for $CO_2$ capture in combustion fumes or for deacidizing a natural gas, one of the following compounds can be preferably used:

-4-methyl-4H-1,2,4-triazole-3-thiol

-1H-1,2,4-triazole-3-thiol

-1H-5-mercapto-1,2,3-triazole

-5-mercapto-1-methyltetrazole, also called 1-methyl-1H-tetrazole-5-thiol

-5-methyl-4H-1,2,4-triazole-3-thiol

-4-isopropyl-4H-1,2,4-triazole-3-thiol

-4-phenyl-4H-1,2,4-triazole-3-thiol

-1-[2-(dimethylamino)ethyl]-1H-tetrazole-5-thiol as well as their salts such as, for example, sodium, potassium or ammonium salts, like for example:

-4-methyl-4H-1,2,4-triazole-3-thiol sodium salt

-1H-1,2,4-triazole-3-thiol sodium salt

-1H-5-mercapto-1,2,3-triazole sodium salt

-5-mercapto-1-methyltetrazole sodium salt, also called 1-methyl-1H-tetrazole-5-thiol sodium salt 5-methyl-4H-1,2,4-triazole-3-thiol sodium salt,
4-isopropyl-4H-1,2,4-triazole-3-thiol sodium salt,
4-phenyl-4H-1,2,4-triazole-3-thiol sodium salt,
5-methyl-4H-1,2,4-triazole-3-thiol potassium salt,
4-methyl-4H-1,2,4-triazole-3-thiol potassium salt,
1H-1,2,4-triazole-3-thiol potassium salt,
4-isopropyl-4H-1,2,4-triazole-3-thiol potassium salt,
4-phenyl-4H-1,2,4-triazole-3-thiol potassium salt,
5-mercapto-1-methyltetrazole potassium salt, also called 1-methyl-1H-tetrazole-5-thiol potassium salt.

Preferably, according to the invention, 1H-1,2,4-triazole-3-thiol sodium salt, 4-methyl-4H-1,2,4-triazole-3-thiol sodium salt, 4-methyl-4H-1,2,4-triazole-3-thiol, 5-methyl-4H-1,2,4-triazole-3-thiol, 4-isopropyl-4H-1,2,4-triazole-3-thiol, 4-phenyl-4H-1,2,4-triazole-3-thiol, 1-methyl-1H-tetrazole-5-thiol or 1-[2-(dimethylamino)ethyl]-1H-tetrazole-5-thiol are used to limit the degradation of an amine, in particular MEA, in aqueous solution used for deacidizing a gaseous effluent, notably within the context of the capture of $CO_2$ contained in combustion fumes.

Preferably, according to the invention, 4-methyl-4H-1,2,4-triazole-3-thiol is used to limit the degradation of an amine, in particular DEA, in aqueous solution used for deacidizing a gaseous effluent, notably within the context of natural gas deacidizing.

Preferably, according to the invention, 4-methyl-4H-1,2,4-triazole-3-thiol is used to limit the degradation of an amine, in particular AMP, in aqueous solution used for deacidizing a gaseous effluent, notably within the context of the capture of $CO_2$ contained in combustion fumes.

The absorbent solution according to the invention comprises an amount of degradation inhibiting agents defined by the general formula described above. The absorbent solution can contain one or more different degradation inhibiting agents corresponding to said general formula. Furthermore, in the absorbent solution, the degradation inhibiting agents according to the invention can be associated with other degradation inhibiting compounds from different chemical families. According to the invention, the absorbent solution contains between 5 ppm and 5 wt. % degradation inhibiting agents according to the invention, preferably between 50 ppm and 2 wt. %, and an excellent proportion of degradation inhibiting agents in the solution ranges between 100 ppm and 1 wt. %.

The numerical examples hereafter allow to compare and to illustrate the performances of the degradation inhibiting agents according to the invention, in terms of reduction in the degradation of amines in aqueous solution, reduction in the emissions of volatile degradation compounds and possibility of increasing the amine concentration without increasing the degradation thereof.

Example 1

The amines of the absorbent solution can be degraded in a use according to the invention generating consumption of the amine.

The degradation tests on an amine in aqueous solution are carried out according to the method of operation as follows.

100 g solution of 30 wt. % MEA (monoethanolamine) in deionized water are placed in a glass reactor topped by a condenser to prevent water evaporation. The reactor is heated to 80° C. in an electric heating block. The solution is stirred at 1000 rpm by a bar magnet. The presence of counterblades prevents the formation of a vortex. A gas is contacted with the solution by means of a dip tube for 7 days at atmospheric pressure. According to the tests, the nature of the gas contacted with the solution is varied. Similarly, the tests are carried out either in the absence or in the presence of various degradation inhibiting agents incorporated in the 0.25 wt. % amine in aqueous solution.

When the test is carried out only in the presence of $CO_2$ and in the absence of oxygen, the gas contacted with the solution is a mixture of 7 Nl/h nitrogen and 0.033 Nl/h $CO_2$ prepared in a mixing chamber. In this case, the gas only comprises $CO_2$ and nitrogen.

When the test is carried out in the presence of $CO_2$ and of oxygen, the gas contacted with the solution is a mixture of 7 Nl/h atmospheric air, i.e. non-purified ambient air, and 0.033 Nl/h $CO_2$ prepared in a mixing chamber. In this case, the gas contains $CO_2$, nitrogen and oxygen, the oxygen content of the gas being about 21%.

A gas chromatography analysis of the solution thus degraded is conducted at the end of the test. The chromatographic method uses a polar column, a carrier gas, helium, an internal standard, triethyleneglycol, and FID (Flame-Induced Detection). This analysis allows to determine the residual MEA concentration and therefore the degradation ratio defined by:

$$\text{Degradation ratio} = \left(1 - \frac{[MEA]_{final}}{[MEA]_{initial}}\right) * 100$$

Table 1 gives the degradation ratios of an aqueous solution of 30 wt. % MEA (monoethanolamine), in the presence of a degradation inhibiting agent or not, subjected to a gas containing nitrogen, $CO_2$ and containing oxygen or not:
  Case No. 1: without oxygen and without additive
  Case No. 2: in the presence of oxygen and without additive
  Case No. 3: in the presence of oxygen and in the presence of a conventional anti-oxygen additive, sodium sulfite ($Na_2SO_3$)
  Case No. 4: in the presence of oxygen and in the presence of an additive according to the invention, 1H-1,2,4-triazole-3-thiol sodium salt,
  Case No. 5: in the presence of oxygen and in the presence of an additive according to the invention, 4-methyl-4H-1,2,4-triazole-3-thiol sodium salt.

TABLE 1

Comparison of the degradation ratios of the 30 wt. % MEA obtained in water at 80° C. in the different cases

| Case | $O_2$ content | Additive name | Degradation ratio |
|---|---|---|---|
| 1 | 0% | — | <3% |
| 2 | 21% | — | 70% |
| 3 | 21% | Sodium sulfite ($Na_2SO_3$) | 71% |
| 4 | 21% | 1H-1,2,4-triazole-3-thiol sodium salt | <3% |
| 5 | 21% | 4-methyl-4H-1,2,4-triazole-3-thiol sodium salt | <3% |

It clearly appears that:
1. The MEA solution is not degraded in the presence of $CO_2$ alone, in the absence of oxygen
2. the degradation of the MEA is attributable to the presence of oxygen
3. in the presence of a conventional reducing anti-oxygen agent such as sodium sulfite, the degradation of the MEA in the presence of oxygen is not reduced
4. in the presence of additives according to the invention, the degradation of the MEA is brought to the level observed in the absence of oxygen, i.e. considered to be zero since below the 3% measurement uncertainty.

In conclusion, the additives according to the invention efficiently combat the effect of oxygen on the degradation of MEA.

Example 2

In particular, the amines can be degraded by oxygen generating the formation of volatile products that are carried along with the gaseous effluents of the process. Thus, for example in the case of post-combustion fumes treatment in a process using an aqueous solution of MEA, large amounts of ammonia form. The ammonia thus formed is discharged to the atmosphere with the treated fumes, which poses environmental protection problems.

Figure 1:
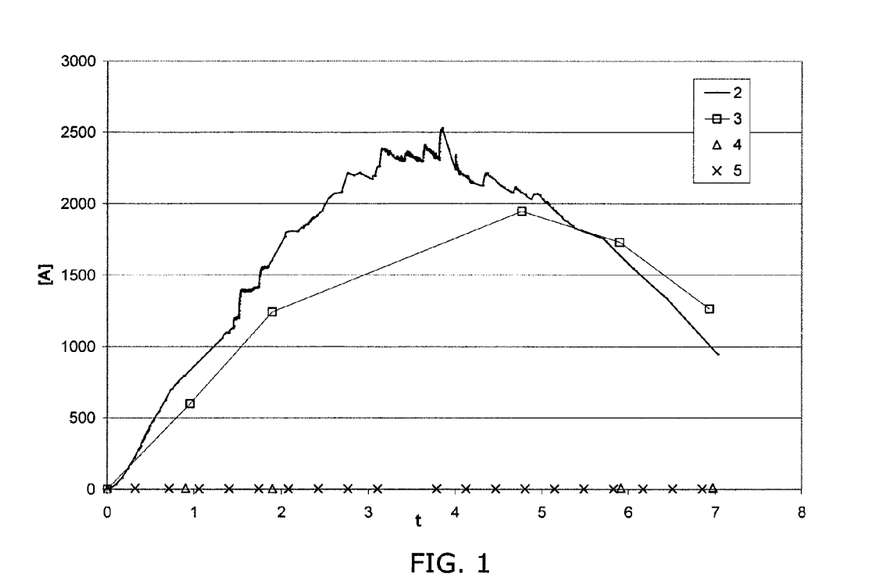
FIGS. 1 to 5 show the proportion of $NH_3$ in the gas phase treated by an absorbent solution depending on the addition or not of degradation inhibiting agents to the absorbent solution and on the proportion of amine in the absorbent solution.

FIG. 1 shows the evolution of the ammonia concentration in the gas leaving the reactor in Cases 2, 3, 4 and 5 defined in Example 1. [A] corresponds to the ammonia concentration in vol. ppm in the gas leaving the reactor, t represents time expressed in days. Cases 2, 3, 4 and 5 are respectively represented by curve 2 in full line, curve 3 with squares, curve 4 with triangles and curve 5 with crosses.

The ammonia concentration of the gas leaving the reactor is determined by means of an in-line analysis by Fourier transform infrared spectrometry.

In the case of the degradation inhibiting agents according to the invention, the $NH_3$ content is below 10 ppm throughout the test (see curves 4 and 5), whereas it reaches nearly 2000 ppm in the case of a conventional anti-oxygen agent (see curve 3), sodium sulfite, and nearly 2500 ppm without a degradation inhibiting agent (see curve 2).

This example clearly shows that the degradation inhibiting agents according to the invention are efficient in reducing volatile degradation compound emissions. Therefore, in an industrial process using an absorbent solution containing degradation inhibiting agents according to the invention, volatile compound emissions at the absorber top are much lower than in the absence of degradation inhibiting agents.

Example 3

This example shows that using amine degradation inhibiting agents allows to increase the amine concentration without increasing the degradation. This example shows the results obtained with an aqueous solution of 40 wt. % MEA.

The degradation tests on an amine in aqueous solution are carried out according to the method of operation as follows.

100 g solution of 40 wt. % MEA in deionized water are placed in a glass reactor topped by a condenser to prevent water evaporation. The reactor is heated to 80° C. in an electric heating block. The solution is stirred at 1000 rpm by a bar magnet. The presence of counterblades prevents the formation of a vortex. A gas is contacted with the solution by means of a dip tube for 7 days at atmospheric pressure. The tests are carried out either in the absence or in the presence of a degradation inhibiting agent incorporated in the 0.25 wt. % amine in aqueous solution.

The test is carried out in the presence of $CO_2$ and of oxygen: the gas contacted with the solution is a mixture of 7 Nl/h atmospheric air, i.e. non-purified ambient air, and 0.033 Nl/h $CO_2$ prepared in a mixing chamber. The gas thus contains $CO_2$, nitrogen and oxygen, the oxygen content of the gas being about 21%.

A gas chromatography analysis of the solution thus degraded is conducted at the end of the test. The chromatographic method uses a polar column, a carrier gas, helium, an internal standard, triethyleneglycol, and FID (Flame-Induced Detection). This analysis allows to determine the residual MEA concentration.

An average rate of degradation throughout the test can thus be calculated:

$$\text{Average degradation rate} = \frac{[MEA]_{initial} - [MEA]_{final}}{\text{test duration}} * \text{mass of solution}$$

Similarly, a degradation ratio can be calculated:

$$\text{Degradation ratio} = \left(1 - \frac{[MEA]_{final}}{[MEA]_{initial}}\right) * 100$$

Table 2 shows the average MEA degradation rates obtained under the same conditions in Case No. 6 with a 40 wt. % MEA without additive and in Case No. 2 with a 30 wt. % MEA without additive defined in Example 1.

TABLE 2

Comparison of the average degradation rates of the 30 wt. % and 40 wt. % MEA in the absence of a degradation inhibiting agent according to the invention

| Case | $O_2$ content | [MEA] in wt. % | Average degradation rate (g/day) |
|---|---|---|---|
| 2 | 21% | 30% | 2.99 |
| 6 | 21% | 40% | 3.72 |

Table 2 confirms that an aqueous solution of 40 wt. % MEA degrades faster than a solution of 30 wt. % MEA. Thus, for the same duration, the mass of MEA degraded is greater in the case of an aqueous solution of 40 wt. % MEA.

Table 3 gives the degradation ratios of an aqueous solution of 40 wt. % MEA in the presence of a degradation inhibiting agent or not:

Case No. 6: without additive
Case No. 7: in the presence of an additive according to the invention, 4-methyl-4H-1,2,4-triazole-3-thiol sodium salt
Case No. 8: in the presence of an additive according to the invention, 4-methyl-4H-1,2,4-triazole-3-thiol
Case No. 9: in the presence of an additive according to the invention, 5-methyl-4H-1,2,4-triazole-3-thiol
Case No. 10: in the presence of an additive according to the invention, 4-isopropyl-4H-1,2,4-triazole-3-thiol
Case No. 11: in the presence of an additive according to the invention, 4-phenyl-4H-1,2,4-triazole-3-thiol
Case No. 12: in the presence of an additive according to the invention, 1-methyl-1H-tetrazole-5-thiol
Case No. 13: in the presence of an additive according to the invention, 1-[2-(dimethylamino)ethyl]-1H-tetrazole-5-thiol

TABLE 3

Comparison of the degradation ratios of the 40 wt. % MEA obtained in water at 80° C. in the absence and in the presence of a degradation inhibiting agent according to the invention

| Case | $O_2$ content | Additive name | Degradation ratio |
|---|---|---|---|
| 6 | 21% | — | 66% |
| 7 | 21% | 4-methyl-4H-1,2,4-triazole-3-thiol sodium salt | <3% |
| 8 | 21% | 4-methyl-4H-1,2,4-triazole-3-thiol | <3% |
| 9 | 21% | 5-methyl-4H-1,2,4-triazole-3-thiol | <3% |
| 10 | 21% | 4-isopropyl-4H-1,2,4-triazole-3-thiol | <3% |
| 11 | 21% | 4-phenyl-4H-1,2,4-triazole-3-thiol | <3% |
| 12 | 21% | 1-methyl-1H-tetrazole-5-thiol | <3% |
| 13 | 21% | 1-[2-(dimethylamino)ethyl]-1H-tetrazole-5-thiol | <3% |

It clearly appears that, in the presence of an additive according to the invention, the degradation of the 40 wt. % MEA in water can be considered to be zero since below the 3% measurement uncertainty.

In conclusion, in the case of MEA, the additives according to the invention allow to increase the amine concentration commonly used by the person skilled in the art without increasing the degradation of the amine.

Example 4

This example shows that using amine degradation inhibiting agents allows to increase the amine concentration without increasing volatile degradation product emissions. This example shows the results obtained with an aqueous solution of 40 wt. % MEA.

Figure 2:
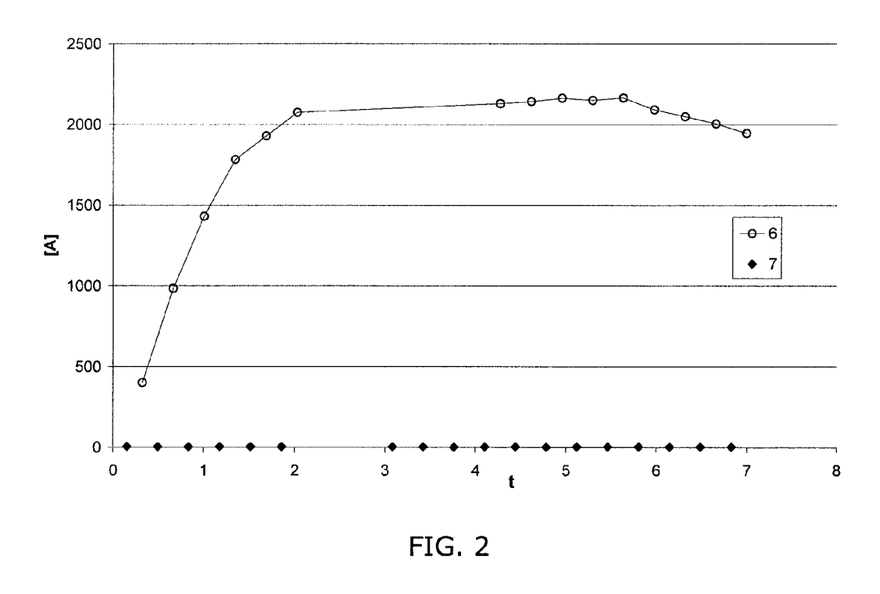

FIG. 2 shows the evolution of the ammonia concentration in the gas leaving the reactor in Cases 6 and 7 defined in Example 3. [A] corresponds to the ammonia concentration in vol. ppm in the gas leaving the reactor, t represents time expressed in days. Cases 6 and 7 are respectively represented by curve 6 with white circles and by curve 7 with black diamonds.

Figure 3:
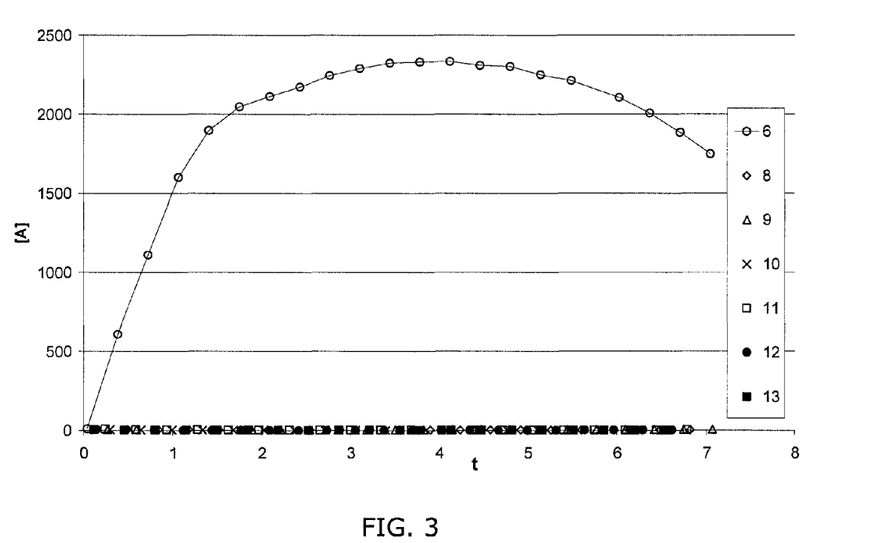

FIG. 3 shows the evolution of the ammonia concentration in the gas leaving the reactor in Cases 8 to 13 defined in Example 3 and in a new evaluation of Case 6. [A] corresponds to the ammonia concentration in vol. ppm in the gas leaving the reactor, t represents time expressed in days. Cases 6, 8, 9, 10, 11, 12 and 13 are respectively represented by curve 6 with white circles, curve 8 with white diamonds, curve 9 with white triangles, curve 10 with crosses, curve 11 with white squares, curve 12 with black circles and curve 13 with black squares.

The ammonia concentration of the gas leaving the reactor is determined by means of an in-line analysis by Fourier transform infrared spectrometry.

In the case of the degradation inhibiting agents according to the invention, the $NH_3$ content is below 10 ppm throughout the test, whereas it rapidly exceeds 2000 ppm without a degradation inhibiting agent. It clearly appears that, in the presence of an additive according to the invention, the ammonia emissions linked with the degradation of the 40 wt. % MEA in water are considerably reduced.

This example clearly shows that, in the case of MEA, the degradation inhibiting agents according to the invention allow to increase the amine concentration commonly used by the person skilled in the art without increasing the ammonia emissions.

Therefore, in an industrial process using an absorbent solution containing degradation inhibiting agents according to the invention, volatile compound emissions at the absorber top are much lower than in the absence of degradation inhibiting agents, even if the amine concentration is increased in relation to the concentration commonly used by the person skilled in the art.

Example 5

The previous examples have shown the efficiency of the degradation inhibiting agents according to the invention in reducing the degradation of amines, in particular in the case of MEA and even with a proportion of 40 wt. % amine. In this example, we show that the degradation inhibiting agents according to the invention are efficient in reducing the degradation of N,N-diethanolamine (DEA), very commonly used for example for natural gas treatment, and of 2-amino-2-methylpropanol-1 (AMP), used for example for $CO_2$ capture in fumes.

This example shows the results obtained with aqueous solutions of 40 wt. % DEA and 40 wt. % AMP.

The degradation tests on an amine in aqueous solution are carried out according to the method of operation as follows.

100 g solution of 40 wt. % amine in deionized water are placed in a glass reactor topped by a condenser to prevent water evaporation. The reactor is heated to 80° C. in an electric heating block. The solution is stirred at 1000 rpm by a bar magnet. The presence of counterblades prevents the formation of a vortex. A gas is contacted with the solution by means of a dip tube for 7 days at atmospheric pressure. The tests are carried out either in the absence or in the presence of a degradation inhibiting agent incorporated in the 0.25 wt. % amine in aqueous solution.

The test is carried out in the presence of $CO_2$ and of oxygen: the gas contacted with the solution is a mixture of 7 Nl/h atmospheric air, i.e. non-purified ambient air, and 0.033 Nl/h $CO_2$ prepared in a mixing chamber. The gas thus contains $CO_2$, nitrogen and oxygen, the oxygen content of the gas being about 21%.

A gas chromatography analysis of the solution thus degraded is conducted at the end of the test. The chromatographic method uses a polar column, a carrier gas, helium, an internal standard, triethyleneglycol, and FID (Flame-Induced Detection). This analysis allows to determine the residual amine concentration and therefore the degradation ratio defined by:

$$\text{Degradation ratio} = \left(1 - \frac{[MEA]_{final}}{[MEA]_{initial}}\right) * 100$$

Table 4 gives the degradation ratios of the DEA and of the AMP in the presence of degradation inhibiting agents or not:

Case No. 14: 40 wt. % DEA without additive
Case No. 15: 40 wt. % DEA in the presence of an additive according to the invention, 4-methyl-4H-1,2,4-triazole-3-thiol
Case No. 16: 40 wt. % AMP without additive
Case No. 17: 40 wt. % AMP in the presence of an additive according to the invention, 4-methyl-4H-1,2,4-triazole-3-thiol.

TABLE 4

Comparison of the degradation ratios of the 40 wt. % DEA and of the 40 wt. % AMP obtained in water at 80° C. in the absence and in the presence of a degradation inhibiting agent according to the invention

| Case | $O_2$ content | Amine | Additive name | Degradation ratio |
| --- | --- | --- | --- | --- |
| 14 | 21% | DEA | — | 44% |
| 15 | 21% | DEA | 4-methyl-4H-1,2,4-triazole-3-thiol | <3% |
| 16 | 21% | AMP | — | 8% |
| 17 | 21% | AMP | 4-methyl-4H-1,2,4-triazole-3-thiol | <3% |

It clearly appears that, in the presence of a degradation inhibiting agent according to the invention, the degradation of the 40 wt. % DEA and of the 40 wt. % AMP in water can be considered to be zero since below the 3% measurement uncertainty.

In conclusion, the degradation inhibiting agents according to the invention efficiently combat the effect of oxygen on the degradation of DEA and AMP, even with high amine concentrations.

Example 6

In particular, the amines can be degraded by oxygen generating the formation of volatile products that are carried along in the gaseous effluents of the process. Thus, for example in the case of DEA and AMP, worrying amounts of ammonia form.

Figure 4:
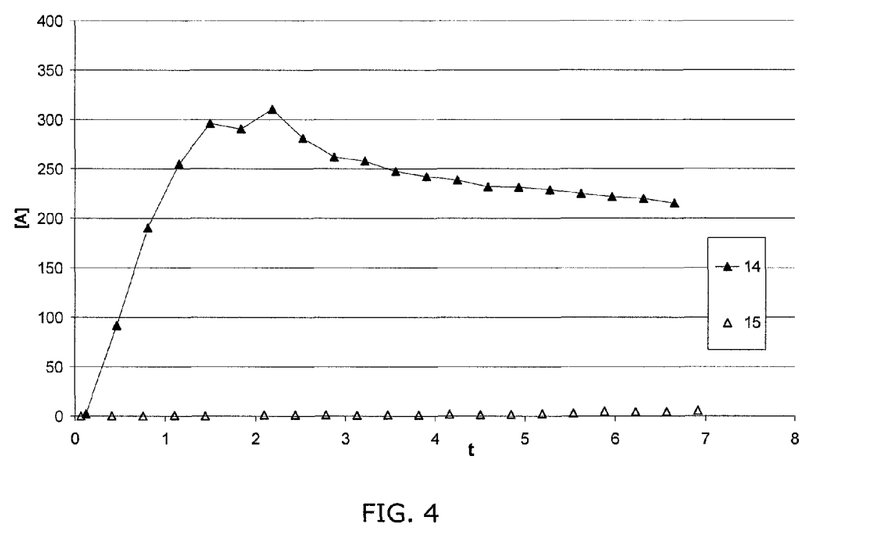

FIG. 4 shows the evolution of the ammonia concentration in the gas leaving the reactor in Cases 14 and 15 defined in Example 5.

Figure 5:
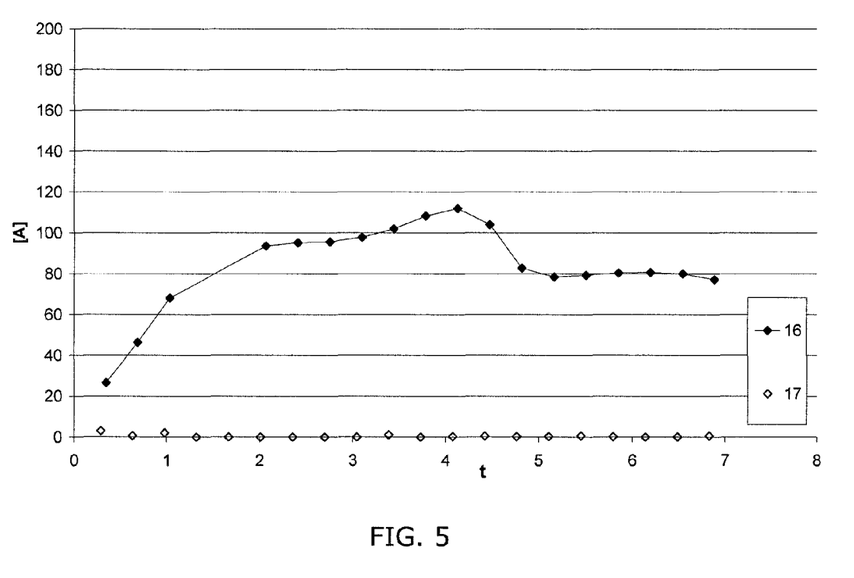

FIG. 5 shows the evolution of the ammonia concentration in the gas leaving the reactor in Cases 16 and 17 defined in Example 5.

[A] corresponds to the ammonia concentration in vol. ppm in the gas leaving the reactor, t represents time expressed in days. Cases 14, 15, 16 and 17 are respectively represented by curve 14 with black triangles, curve 15 with white triangles, curve 16 with black diamonds and curve 17 with white diamonds.

The ammonia concentration of the gas leaving the reactor is determined by means of an in-line analysis by Fourier transform infrared spectrometry.

In the case of the degradation inhibiting agents according to the invention, the $NH_3$ content is still below 10 ppm throughout the test (see curves 15 and 17), whereas it reaches nearly 300 ppm in Case 14 and nearly 110 ppm in Case 16.

This example clearly shows that the degradation inhibiting agents according to the invention are efficient in reducing volatile degradation compound emissions, notably in the case of 40 wt. % DEA in water and 40 wt. % AMP in water. Therefore, in an industrial process using an absorbent solution containing degradation inhibiting agents according to the invention, volatile compound emissions will be much lower than in the absence of degradation inhibiting agents.

The invention claimed is:

1. An absorbent solution for absorbing the acid compounds contained in a gaseous effluent, said solution comprising:
   a) at least one amine,
   b) water,
   c) at least one degradation inhibiting compound for limiting the degradation of said amine, the degradation inhibiting compound being a derivative of a triazole or of a tetrazole, at least one substituent of which comprises a sulfur atom.

2. An absorbent solution as claimed in claim 1, wherein said degradation inhibiting compound meets one of the following general formulas:

wherein radical $R_1$ is selected from among:
   a hydrogen atom,
   a hydrocarbon radical comprising 1 to 12 carbon atoms,
   an amino radical of general formula $-NR_4R_5$ wherein radical $R_4$ and radical $R_5$ are independently selected from among:
      a hydrogen atom,
      a hydrocarbon radical comprising 1 to 12 carbon atoms,
      and wherein each radical $R_2$ and $R_3$ is independently selected from among the following elements:
   a) $-S-X$ wherein radical X is selected from among:
      a hydrogen atom,
      an alkaline or alkaline-earth element,
      a monovalent or multivalent metal,
      an ammonium cation NH4+ or resulting from the protonation of an amine function,
      a phosphonium cation,
      a hydrocarbon radical comprising 1 to 12 carbon atoms,
      a radical selected from among a thiyl-triazole, thio-triazole, thiyl-tetrazole and thio-tetrazole radical,
   b) a hydrogen atom,
   c) a hydroxyl radical,
   d) an amino radical of general formula $-NR_4R_5$ wherein radical $R_4$ and radical $R_5$ are independently selected from among:
      a hydrogen atom,
      a hydrocarbon radical comprising 1 to 12 carbon atoms,
   e) a radical comprising 1 to 12 carbon atoms.

3. An absorbent solution as claimed in claim 2, wherein at least one of radicals $R_1$, $R_2$, $R_3$, $R_4$, $R_5$ and X is a hydrocarbon group containing between 1 and 12 carbon atoms and it additionally contains at least one compound selected from among a heteroatom and a halogen.

4. An absorbent solution as claimed in claim 3, wherein at least one of radicals $R_1$, $R_2$, $R_3$, $R_4$, $R_5$ and X comprises at least one function selected from among the group as follows: a hydroxyl function, a ketone function, a carboxylic function, an amine function and a nitrile function.

5. An absorbent solution as claimed in claim 2, wherein at least two radicals selected from among $R_1$, $R_2$, $R_3$, $R_4$, $R_5$ and X are hydrocarbon groups bonded by a covalent bond so as to form a ring made up of 5, 6, 7 or 8 atoms.

6. An absorbent solution as claimed in claim 1, wherein the solution comprises between 10 wt. % and 99 wt. % amine, between 1 wt. % and 90 wt. % water, and between 5 ppm and 5 wt. % degradation inhibiting compound.

7. An absorbent solution as claimed in claim 1, wherein the degradation inhibiting compound is selected from among the group consisting of: 1H-1,2,4-triazole-3-thiol, a 1H-1,2,4-triazole-3-thiol salt, 5-phenyl-1H-1,2,4-triazole-3-thiol, a 5-phenyl-1H-1,2,4-triazole-3-thiol salt, 5-(4-pyridyl)-1H-1,2,4-triazole-3-thiol, a 5-(4-pyridyl)-1H-1,2,4-triazole-3-thiol salt, 5-(3-pyridyl)-1H-1,2,4-triazole-3-thiol, a 5-(3-pyridyl)-1H-1,2,4-triazole-3-thiol salt, 4-methyl-4H-1,2,4-triazole-3-thiol, a 4-methyl-4H-1,2,4-triazole-3-thiol salt, 4-methyl-5-(2-thienyl)-4H-1,2,4-triazole-3-thiol, a 4-methyl-5-(2-thienyl)-4H-1,2,4-triazole-3-thiol salt, 4-methyl-5-(3-thienylmethyl)-4H-1,2,4-triazole-3-thiol, a 4-methyl-5-(3-thienylmethyl)-4H-1,2,4-triazole-3-thiol salt, 4-cyclohexyl-5-sulfanyl-4H-1,2,4-triazole-3-01, a 4-cyclohexyl-5-sulfanyl-4H-1,2,4-triazole-3-ol salt, 3-amino-1,2,4-triazole-5-thiol, a 3-amino-1,2,4-triazole-5-thiol salt, 4-amino-4H-1,2,4-triazole-3,5-dithiol, a 4-amino-4H-1,2,4-triazole-3,5-dithiol salt, [1,2,4]triazolo[4,3-a]pyridine-3-thiol, a [1,2,4]triazolo[4,3-a]pyridine-3-thiol salt, 1H-5-mercapto-1,2,3-triazole, a 1H-5-mercapto-1,2,3-triazole salt, 1-methyl-1H-tetrazole-5-thiol, a 1-methyl-1H-tetrazole-5-thiol salt, 1-ethyl-1H-tetrazole-5-thiol, a 1-ethyl-1H-tetrazole-5-thiol salt, 1-phenyl-1H-tetrazole-5-thiol, a 1-phenyl-1H-tetrazole-5-thiol salt, 1-(4-hydroxyphenyl)-1H-tetrazole-5-thiol, a 1-(4-hydroxyphenyl)-1H-tetrazole-5-thiol salt, 5-mercapto-1-tetrazolacetic acid, a 5-mercapto-1-tetrazolacetic acid salt, 1-[2-(dimethylamino)ethyl]-1H-tetrazole-5-thiol, a 1-[2-(dimethylamino)ethyl]-1H-tetrazole-5-thiol salt, 3-amino-5-methylthio-1H-1,2,4-triazole, a 3-amino-5-methylthio-1H-1,2,4-triazole salt, 5-(methylthio)-1H-tetrazole, a 5-(methylthio)-1H-tetrazole salt, 5-(ethylthio)-1H-tetrazole, a 5-(ethylthio)-1H-tetrazole salt, 1-methyl-5-(methylthio)-1H-tetrazole, a 1-methyl-5-(methylthio)-1H-tetrazole salt, 4-phenyl-4H-1,2,4-triazole-3-thiol, a 4-phenyl-4H-1,2,4-triazole-3-thiol salt, 5-methyl-4H-1,2,4-triazole-3-thiol, a 5-methyl-4H-1,2,4-triazole-3-thiol salt, 5-(trifluoromethyl)-2,4-dihydro-3H-1,2,4-triazole-3-thione, a 5-(trifluoromethyl)-2,4-dihydro-3H-1,2,4-triazole-3-thione salt, 4-isopropyl-4H-1,2,4-triazole-3-thiol and a 4-isopropyl-4H-1,2,4-triazole-3-thiol salt.

8. An absorbent solution as claimed in claim 1, wherein the amine is selected from the group consisting of: N,N,N',N',N"-pentamethyldiethylene-triamine, piperazine, monoethanolamine, diethanolamine, methyldiethanolamine, diisopropanolamine, diglycolamine, 2-amino-2-methylpropanol-1, a glycine salt and a taurine salt.

9. An absorbent solution as claimed in claim 1, wherein the amine is selected from among monoethanolamine, diethanolamine and 2-amino-2-methylpropanol-1, and wherein the degradation inhibiting compound is selected from among: 4-methyl-4H-1,2,4-triazole-3-thiol, 1H-1,2,4-triazole-3-thiol, 1H-5-mercapto-1,2,3-triazole, 5-mercapto-1-methyltetrazole, 5-methyl-4H-1,2,4-triazole-3-thiol, 4-isopropyl-4H-1,2,4-triazole-3-thiol, 4-phenyl-4H-1,2,4-triazole-3-thiol, 1-[2-(dimethylamino)ethyl]-1H-tetrazole-5-thiol, 4-methyl-4H-1,2,4-triazole-3-thiol sodium salt, 1H-1,2,4-triazole-3-thiol sodium salt, 1H-5-mercapto-1,2,3-triazole sodium salt, 5-mercapto-1-methyltetrazole sodium salt, 5-methyl-4H-1,2,4-triazole-3-thiol sodium salt, 4-isopropyl-4H-1,2,4-triazole-3-thiol sodium salt, 4-phenyl-4H-1,2,4-triazole-3-thiol sodium salt, 5-methyl-4H-1,2,4-triazole-3-thiol potassium salt, 4-methyl-4H-1,2,4-triazole-3-thiol potassium salt, 1H-1,2,4-triazole-3-thiol potassium salt, 4-isopropyl-4H-1,2,4-triazole-3-thiol potassium salt, 4-phenyl-4H-1,2,4-triazole-3-thiol potassium salt and 5-mercapto-1-methyltetrazole potassium salt.

10. An absorbent solution as claimed in claim 8, comprising at least 39 wt. % monoethanolamine.

11. A method for absorbing acid compounds contained in a gaseous effluent, wherein the gaseous effluent is contacted with an aqueous solution comprising at least one amine, and wherein the degradation of said amine is controlled by introducing at least one degradation inhibiting compound derived from a triazole or from a tetrazole, comprising at least one substituent containing a sulfur atom.

12. A method as claimed in claim 11, wherein the aqueous solution is used for absorbing acid compounds contained in one of the effluents from the group consisting of natural gas, combustion fumes, syngases, refinery gases, Claus tail gases, biomass fermentation gases, cement plant gases and incinerator fumes.

13. A method as claimed in claim 12, wherein the gaseous effluent comprises at least 500 vol. ppm oxygen.

14. A method as claimed in claim 11, wherein at least one degradation inhibiting compound selected from the following group is added to the aqueous solution: 1H-1,2,4-triazole-3-thiol, a 1H-1,2,4-triazole-3-thiol salt, 5-phenyl-1H-1,2,4-triazole-3-thiol, a 5-phenyl-1H-1,2,4-triazole-3-thiol salt, 5-(4-pyridyl)-1H-1,2,4-triazole-3-thiol, a 5-(4-pyridyl)-1H-1,2,4-triazole-3-thiol salt, 5-(3-pyridyl)-1H-1,2,4-triazole-3-thiol, a 5-(3-pyridyl)-1H-1,2,4-triazole-3-thiol salt, 4-methyl-4H-1,2,4-triazole-3-thiol, a 4-methyl-4H-1,2,4-triazole-3-thiol salt, 4-methyl-5-(2-thienyl)-4H-1,2,4-triazole-3-thiol, a 4-methyl-5-(2-thienyl)-4H-1,2,4-triazole-3-thiol salt, 4-methyl-5-(3-thienylmethyl)-4H-1,2,4-triazole-3-thiol, a 4-methyl-5-(3-thienylmethyl)-4H-1,2,4-triazole-3-thiol salt, 4-cyclohexyl-5-sulfanyl-4H-1,2,4-triazole-3-ol, a 4-cyclohexyl-5-sulfanyl-4H-1,2,4-triazole-3-ol salt, 3-amino-1,2,4-triazole-5-thiol, a 3-amino-1,2,4-triazole-5-thiol salt, 4-amino-4H-1,2,4-triazole-3,5-dithiol, a 4-amino-4H-1,2,4-triazole-3,5-dithiol salt, [1,2,4]triazolo[4,3-a]pyridine-3-thiol, a [1,2,4]triazolo[4,3-a]pyridine-3-thiol salt, 1H-5-mercapto-1,2,3-triazole, a 1H-5-mercapto-1,2,3-triazole salt, 1-methyl-1H-tetrazole-5-thiol, a 1-methyl-1H-tetrazole-5-thiol salt, 1-ethyl-1H-tetrazole-5-thiol, a 1-ethyl-1H-tetrazole-5-thiol salt, 1-phenyl-1H-tetrazole-5-thiol, a 1-phenyl-1H-tetrazole-5-thiol salt, 1-(4-hydroxyphenyl)-1H-tetrazole-5-thiol, a 1-(4-hydroxyphenyl)-1H-tetrazole-5-thiol salt, 5-mercapto-1-tetrazolacetic acid, a 5-mercapto-1-tetrazolacetic acid salt, 1-[2-(dimethylamino)ethyl]-1H-tetrazole-5-thiol, a 1-[2-(dimethylamino)ethyl]-1H-tetrazole-5-thiol salt, 3-amino-5-methylthio-1H-1,2,4-triazole, a 3-amino-5-methylthio-1H-1,2,4-triazole salt, 5-(methylthio)-1H-tetrazole, a 5-(methylthio)-1H-tetrazole salt, 5-(ethylthio)-1H-tetrazole, a 5-(ethylthio)-1H-tetrazole salt, 1-methyl-5-(methylthio)-1H-tetrazole, a 1-methyl-5-(methylthio)-1H-tetrazole salt, 4-phenyl-4H-1,2,4-triazole-3-thiol, a 4-phenyl-4H-1,2,4-triazole-3-thiol salt, 5-methyl-4H-1,2,4-triazole-3-thiol, a 5-methyl-4H-1,2,4-triazole-3-thiol salt, 5-(trifluoromethyl)-2,4-dihydro-3H-1,2,4-triazole-3-thione, a 5-(trifluoromethyl)-2,4-dihydro-3H-1,2,4-triazole-3-thione salt, 4-isopropyl-4H-1,2,4-triazole-3-thiol and a 4-isopropyl-4H-1,2,4-triazole-3-thiol salt.

15. A method as claimed in claim 11 wherein, in order to limit degradation of one of the amines selected from among monoethanolamine, diethanolamine and 2-amino-2-methylpropanol-1, the amine being in aqueous solution and used for capturing the $CO_2$ from combustion fumes, at least one degradation inhibiting compound selected from the group consisting of the following elements is added to the aqueous solution: 4-methyl-4H-1,2,4-triazole-3-thiol, 1H-1,2,4-triazole-3-thiol, 1H-5-mercapto-1,2,3-triazole, 5-mercapto-1-methyl-tetrazole, 5-methyl-4H-1,2,4-triazole-3-thiol, 4-isopropyl-4H-1,2,4-triazole-3-thiol, 4-phenyl-4H-1,2,4-triazole-3-thiol, 1-[2-(dimethylamino)ethyl]-1H-tetrazole-5-thiol, 4-methyl-4H-1,2,4-triazole-3-thiol sodium salt, 1H-1,2,4-triazole-3-thiol sodium salt, 1H-5-mercapto-1,2,3-triazole sodium salt, 5-mercapto-1-methyltetrazole sodium salt, 5-methyl-4H-1,2,4-triazole-3-thiol sodium salt, 4-isopropyl-4H-1,2,4-triazole-3-thiol sodium salt, 4-phenyl-4H-1,2,4-triazole-3-thiol sodium salt, 5-methyl-4H-1,2,4-triazole-3-thiol potassium salt, 4-methyl-4H-1,2,4-triazole-3-thiol potassium salt, 1H-1,2,4-triazole-3-thiol potassium salt, 4-isopropyl-4H-1,2,4-triazole-3-thiol potassium salt, 4-phenyl-4H-1,2,4-triazole-3-thiol potassium salt and 5-mercapto-1-methyltetrazole potassium salt.

* * * * *